(12) United States Patent
Gindele (10) Patent No.: US 8,380,312 B2
(45) Date of Patent: Feb. 19, 2013

(54) MULTI-ZONE STIMULATION IMPLANT SYSTEM AND METHOD

(75) Inventor: Paul J. Gindele, Albertville, MN (US)

(73) Assignee: AMS Research Corporation, Minnetonka, MN (US)

( * ) Notice: Subject to any disclaimer, the term of this patent is extended or adjusted under 35 U.S.C. 154(b) by 124 days.

(21) Appl. No.: 12/982,657

(22) Filed: Dec. 30, 2010

(65) Prior Publication Data

US 2011/0160793 A1  Jun. 30, 2011

Related U.S. Application Data

(60) Provisional application No. 61/291,368, filed on Dec. 31, 2009, provisional application No. 61/291,362, filed on Dec. 31, 2009.

(51) Int. Cl.
*A61N 1/00* (2006.01)
(52) U.S. Cl. ........................................... 607/40
(58) Field of Classification Search ............... 607/40, 607/41, 59, 3, 118; 606/127; 600/30
See application file for complete search history.

(56) References Cited

U.S. PATENT DOCUMENTS

| | | |
|---|---|---|
| 2,816,997 A | 12/1957 | Conrad |
| 3,628,538 A | 12/1971 | Vincent et al. |
| 3,640,284 A | 2/1972 | De Langis |
| 3,646,940 A | 3/1972 | Timm et al. |
| 3,650,276 A | 3/1972 | Burghele et al. |
| 3,662,758 A | 5/1972 | Glover |
| 3,667,477 A | 6/1972 | Susset et al. |
| 3,831,588 A | 8/1974 | Rindner |
| 3,866,613 A | 2/1975 | Kenny et al. |
| 3,870,051 A | 3/1975 | Brindley |
| 3,926,178 A | 12/1975 | Feldzamen |
| 3,941,136 A | 3/1976 | Bucalo |
| 3,983,865 A | 10/1976 | Shepard |
| 3,983,881 A | 10/1976 | Wickham |
| 3,999,555 A | 12/1976 | Person |
| 4,010,758 A | 3/1977 | Rockland et al. |
| 4,023,562 A | 5/1977 | Hynecek et al. |
| 4,023,574 A | 5/1977 | Nemec |
| 4,030,509 A | 6/1977 | Heilman et al. |
| 4,044,774 A | 8/1977 | Corbin et al. |
| 4,106,511 A | 8/1978 | Erlandsson |
| 4,136,684 A | 1/1979 | Scattergood et al. |
| 4,139,006 A | 2/1979 | Corey |
| 4,153,059 A | 5/1979 | Fravel et al. |

(Continued)

FOREIGN PATENT DOCUMENTS

DE  8506522.6  6/1985
EP  0245547  11/1987

(Continued)

OTHER PUBLICATIONS

O'Donnell, Pat D., *Urinary Incontinence,* Mosby Year Book, Inc pp. 197-202 (1997).

(Continued)

*Primary Examiner* — George Manuel
*Assistant Examiner* — Robert N Wieland
(74) *Attorney, Agent, or Firm* — Gregory L. Koeller; Kimberly K. Baxter (57) ABSTRACT

Various embodiments of an implant system are provided. The implant, such as a mesh implant, can include a support structure, e.g., mesh sling or implant, one or more stimulation elements (e.g., leads), and an energizing element. Leads or electrodes can be positioned in desired stimulation zones of the implant. As such, the implant can include multiple electrically isolated mesh electrode pads or regions.

12 Claims, 5 Drawing Sheets

U.S. PATENT DOCUMENTS

| | | |
|---|---|---|
| 4,157,087 A | 6/1979 | Miller et al. |
| 4,165,750 A | 8/1979 | Aleev et al. |
| 4,177,819 A | 12/1979 | Kofsky et al. |
| 4,222,377 A | 9/1980 | Burton |
| 4,222,385 A | 9/1980 | Backhouse |
| 4,290,420 A | 9/1981 | Manetta |
| 4,387,719 A | 6/1983 | Plevnik |
| 4,402,328 A | 9/1983 | Doring |
| 4,406,288 A | 9/1983 | Horwinski et al. |
| 4,407,296 A | 10/1983 | Anderson |
| 4,414,986 A | 11/1983 | Dickhudt et al. |
| 4,431,001 A | 2/1984 | Hakansson et al. |
| 4,432,372 A | 2/1984 | Monroe |
| 4,457,299 A | 7/1984 | Cornwell |
| 4,492,233 A | 1/1985 | Petrofsky et al. |
| 4,515,167 A | 5/1985 | Hochman |
| 4,542,753 A | 9/1985 | Brenman et al. |
| 4,550,737 A | 11/1985 | Osypka |
| 4,556,061 A | 12/1985 | Barreras et al. |
| 4,568,339 A | 2/1986 | Steer |
| 4,569,351 A | 2/1986 | Tang |
| 4,571,749 A | 2/1986 | Fischell |
| 4,580,578 A | 4/1986 | Barsom |
| 4,585,005 A | 4/1986 | Lue et al. |
| 4,590,949 A | 5/1986 | Pohndorf |
| 4,602,624 A | 7/1986 | Naples et al. |
| 4,607,639 A | 8/1986 | Tanagho et al. |
| 4,628,942 A | 12/1986 | Sweeney et al. |
| 4,688,575 A | 8/1987 | DuVall |
| 4,703,755 A | 11/1987 | Tanagho et al. |
| 4,730,389 A | 3/1988 | Baudino |
| 4,731,083 A | 3/1988 | Fischell |
| 4,735,205 A | 4/1988 | Chachques et al. |
| 4,739,764 A | 4/1988 | Lue et al. |
| 4,750,494 A | 6/1988 | King |
| 4,771,779 A | 9/1988 | Tanagho et al. |
| 4,785,828 A | 11/1988 | Maurer |
| 4,825,876 A | 5/1989 | Beard |
| 4,846,191 A | 7/1989 | Brockway et al. |
| 4,873,986 A | 10/1989 | Wallace |
| 4,878,889 A | 11/1989 | Polyak |
| 4,881,526 A | 11/1989 | Johnson et al. |
| 4,913,164 A | 4/1990 | Greene et al. |
| 4,941,874 A | 7/1990 | Sandow et al. |
| 5,013,292 A | 5/1991 | Lemay |
| 5,019,032 A | 5/1991 | Robertson |
| 5,037,488 A | 8/1991 | Wienand |
| 5,082,006 A | 1/1992 | Jonasson |
| 5,094,242 A | 3/1992 | Gleason et al. |
| 5,103,835 A | 4/1992 | Yamada et al. |
| 5,112,344 A | 5/1992 | Petros |
| 5,113,868 A | 5/1992 | Wise et al. |
| 5,144,948 A | 9/1992 | Andersson et al. |
| 5,184,619 A | 2/1993 | Austin |
| 5,186,170 A | 2/1993 | Varrichio et al. |
| 5,193,539 A | 3/1993 | Schulman et al. |
| 5,193,540 A | 3/1993 | Schulman et al. |
| 5,199,430 A | 4/1993 | Fang et al. |
| 5,201,865 A | 4/1993 | Kuehn |
| 5,207,103 A | 5/1993 | Wise et al. |
| 5,211,175 A | 5/1993 | Gleason et al. |
| 5,233,982 A | 8/1993 | Kohl |
| 5,235,980 A | 8/1993 | Varrichio et al. |
| 5,285,781 A | 2/1994 | Brodard |
| 5,291,902 A | 3/1994 | Carman |
| 5,300,093 A | 4/1994 | Koestner et al. |
| 5,312,439 A | 5/1994 | Loeb |
| 5,314,458 A | 5/1994 | Najafi et al. |
| 5,324,316 A | 6/1994 | Schulman et al. |
| 5,324,323 A | 6/1994 | Bui |
| 5,324,324 A | 6/1994 | Vachon et al. |
| 5,324,326 A | 6/1994 | Lubin |
| 5,330,505 A | 7/1994 | Cohen |
| 5,330,507 A | 7/1994 | Schwartz |
| 5,344,439 A | 9/1994 | Otten |
| 5,358,514 A | 10/1994 | Schulman et al. |
| 5,366,493 A | 11/1994 | Scheiner et al. |
| 5,370,670 A | 12/1994 | Chancellor |
| 5,385,577 A | 1/1995 | Maurer et al. |
| 5,391,191 A | 2/1995 | Holmstrom |
| 5,405,367 A | 4/1995 | Schulman et al. |
| 5,411,538 A | 5/1995 | Lin |
| 5,411,548 A | 5/1995 | Carman et al. |
| 5,417,226 A | 5/1995 | Juma |
| 5,423,329 A | 6/1995 | Ergas |
| 5,425,751 A | 6/1995 | Baeten et al. |
| 5,431,686 A | 7/1995 | Kroll et al. |
| 5,452,719 A | 9/1995 | Eisman et al. |
| 5,484,445 A | 1/1996 | Knuth |
| 5,486,201 A | 1/1996 | Canfield |
| 5,508,476 A | 4/1996 | Dickenson |
| 5,518,504 A | 5/1996 | Polyak |
| 5,520,606 A | 5/1996 | Schoolman et al. |
| 5,522,266 A | 6/1996 | Nicholson et al. |
| 5,562,717 A | 10/1996 | Tippey et al. |
| 5,564,434 A | 10/1996 | Halperin et al. |
| 5,566,680 A | 10/1996 | Urion et al. |
| 5,568,815 A | 10/1996 | Raynes et al. |
| 5,569,351 A | 10/1996 | Menta et al. |
| 5,571,148 A | 11/1996 | Loeb et al. |
| 5,611,515 A | 3/1997 | Benderev et al. |
| 5,611,768 A | 3/1997 | Tutrone, Jr. |
| 5,611,769 A | 3/1997 | Monroe |
| 5,634,462 A | 6/1997 | Tyler et al. |
| 5,658,321 A | 8/1997 | Fayram et al. |
| 5,693,000 A | 12/1997 | Crosby et al. |
| 5,702,428 A | 12/1997 | Tippey et al. |
| 5,722,997 A | 3/1998 | Nedungadi et al. |
| 5,726,624 A | 3/1998 | Caffee et al. |
| 5,752,978 A | 5/1998 | Chancellor |
| 5,766,229 A | 6/1998 | Bornzin |
| 5,769,873 A | 6/1998 | Zadeh |
| 5,785,666 A | 7/1998 | Costello et al. |
| 5,803,897 A | 9/1998 | Mooreville et al. |
| 5,807,265 A | 9/1998 | Itoigawa et al. |
| 5,807,397 A | 9/1998 | Barreras |
| 5,824,027 A | 10/1998 | Hoffer et al. |
| 5,833,595 A | 11/1998 | Lin |
| 5,836,886 A | 11/1998 | Itoigawa et al. |
| 5,836,994 A | 11/1998 | Bourgeois |
| 5,842,478 A | 12/1998 | Benderev et al. |
| 5,851,226 A | 12/1998 | Skubitz et al. |
| 5,860,425 A | 1/1999 | Benderev et al. |
| 5,876,353 A | 3/1999 | Riff |
| 5,899,909 A | 5/1999 | Claren et al. |
| 5,902,331 A | 5/1999 | Bonner et al. |
| 5,927,282 A | 7/1999 | Lenker et al. |
| 5,931,864 A | 8/1999 | Chastain et al. |
| 5,941,903 A | 8/1999 | Zhu et al. |
| 5,954,761 A | 9/1999 | Machek et al. |
| 5,957,920 A | 9/1999 | Baker |
| 5,957,965 A | 9/1999 | Moumane et al. |
| 5,963,097 A | 10/1999 | Garachtchenko et al. |
| 5,969,591 A | 10/1999 | Fung |
| 5,978,712 A | 11/1999 | Suda et al. |
| 5,984,711 A | 11/1999 | Woodward |
| 5,984,854 A | 11/1999 | Ishikawa et al. |
| 6,002,964 A | 12/1999 | Feler et al. |
| 6,006,135 A | 12/1999 | Kast et al. |
| 6,019,729 A | 2/2000 | Itoigawa et al. |
| 6,026,326 A | 2/2000 | Bardy |
| 6,027,456 A | 2/2000 | Feler et al. |
| 6,038,463 A | 3/2000 | Laske et al. |
| 6,039,686 A | 3/2000 | Kovac |
| 6,042,534 A | 3/2000 | Gellman et al. |
| 6,051,017 A | 4/2000 | Loeb et al. |
| 6,055,456 A | 4/2000 | Gerber |
| 6,061,596 A | 5/2000 | Richmond et al. |
| 6,078,840 A | 6/2000 | Stokes |
| 6,104,955 A | 8/2000 | Bourgeois |
| 6,104,960 A | 8/2000 | Duysens et al. |
| 6,110,101 A | 8/2000 | Tihon et al. |
| 6,128,531 A | 10/2000 | Campbell-Smith |
| 6,128,536 A | 10/2000 | Noack et al. |
| 6,129,658 A | 10/2000 | Delfino et al. |
| 6,131,575 A | 10/2000 | Lenker et al. |
| 6,135,945 A | 10/2000 | Sultan |

| | | | |
|---|---|---|---|
| 6,141,594 A | 10/2000 | Flynn et al. | |
| 6,161,029 A | 12/2000 | Spreigl et al. | |
| 6,178,356 B1 | 1/2001 | Chastain et al. | |
| 6,185,452 B1 | 2/2001 | Schulman et al. | |
| 6,208,894 B1 | 3/2001 | Schulman et al. | |
| 6,221,024 B1 | 4/2001 | Miesel | |
| 6,238,423 B1 | 5/2001 | Bardy | |
| 6,240,315 B1 | 5/2001 | Mo et al. | |
| 6,240,316 B1 | 5/2001 | Richmond et al. | |
| 6,243,607 B1 | 6/2001 | Mintchev et al. | |
| 6,248,083 B1 | 6/2001 | Smith et al. | |
| 6,253,108 B1 | 6/2001 | Rosborough et al. | |
| 6,259,949 B1 | 7/2001 | Rosborough et al. | |
| 6,263,241 B1 | 7/2001 | Rosborough et al. | |
| 6,266,557 B1 | 7/2001 | Roe et al. | |
| 6,266,564 B1 | 7/2001 | Hill et al. | |
| 6,304,786 B1 | 10/2001 | Heil et al. | |
| 6,328,686 B1 | 12/2001 | Kovac | |
| 6,328,687 B1 | 12/2001 | Karram et al. | |
| 6,341,236 B1 | 1/2002 | Osorio et al. | |
| 6,354,991 B1 | 3/2002 | Gross et al. | |
| 6,356,788 B2 | 3/2002 | Boveja et al. | |
| 6,360,750 B1 | 3/2002 | Gerber et al. | |
| 6,366,814 B1 | 4/2002 | Boveja et al. | |
| 6,382,214 B1 | 5/2002 | Raz et al. | |
| 6,393,323 B1 | 5/2002 | Sawan | |
| 6,397,109 B1 | 5/2002 | Cammilli et al. | |
| 6,407,308 B1 | 6/2002 | Roe et al. | |
| 6,418,930 B1 | 7/2002 | Fowler | |
| 6,477,414 B1 | 11/2002 | Silvian | |
| 6,478,727 B2 | 11/2002 | Scetbon | |
| 6,505,074 B2 | 1/2003 | Boveja | |
| 6,505,082 B1 | 1/2003 | Scheiner et al. | |
| 6,572,543 B1 | 6/2003 | Christopherson et al. | |
| 6,582,441 B1 | 6/2003 | He et al. | |
| 6,585,660 B2 | 7/2003 | Dorando et al. | |
| 6,600,956 B2 | 7/2003 | Maschino et al. | |
| 6,612,977 B2 | 9/2003 | Staskin et al. | |
| 6,641,524 B2 | 11/2003 | Kovac | |
| 6,641,525 B2 | 11/2003 | Rocheleau et al. | |
| 6,648,921 B2 | 11/2003 | Anderson et al. | |
| 6,650,943 B1 | 11/2003 | Whitehurst et al. | |
| 6,652,449 B1 | 11/2003 | Gross et al. | |
| 6,652,450 B1 | 11/2003 | Neisz et al. | |
| 6,652,499 B1 | 11/2003 | Edgren et al. | |
| 6,658,297 B2 | 12/2003 | Loeb | |
| 6,659,936 B1 | 12/2003 | Furness et al. | |
| 6,691,711 B2 | 2/2004 | Raz et al. | |
| 6,712,772 B2 | 3/2004 | Cohen et al. | |
| 6,735,474 B1 | 5/2004 | Loeb et al. | |
| 6,738,674 B2 | 5/2004 | Osypka | |
| 6,745,079 B2 | 6/2004 | King | |
| 6,764,472 B1 | 7/2004 | Burke et al. | |
| 6,802,807 B2 | 10/2004 | Anderson et al. | |
| 6,836,684 B1 | 12/2004 | Rijkhoff et al. | |
| 6,862,480 B2 | 3/2005 | Cohen et al. | |
| 6,885,894 B2 | 4/2005 | Stessman | |
| 6,896,651 B2 | 5/2005 | Gross et al. | |
| 6,911,003 B2 | 6/2005 | Anderson et al. | |
| 6,915,162 B2 | 7/2005 | Noren et al. | |
| 6,941,171 B2 | 9/2005 | Mann et al. | |
| 6,952,613 B2 | 10/2005 | Swoyer et al. | |
| 6,964,643 B2 | 11/2005 | Hovland et al. | |
| 6,964,699 B1 | 11/2005 | Carns et al. | |
| 6,971,393 B1 | 12/2005 | Mamo et al. | |
| 7,011,622 B2 | 3/2006 | Kuyava et al. | |
| 7,025,063 B2 | 4/2006 | Snitkin et al. | |
| 7,054,689 B1 | 5/2006 | Whitehurst et al. | |
| 7,070,556 B2 | 7/2006 | Anderson et al. | |
| 7,079,882 B1 | 7/2006 | Schmidt | |
| 7,120,499 B2 | 10/2006 | Thrope et al. | |
| 7,203,548 B2 | 4/2007 | Whitehurst et al. | |
| 7,217,237 B2 | 5/2007 | Wassemann et al. | |
| 7,267,645 B2 | 9/2007 | Anderson et al. | |
| 7,292,890 B2 | 11/2007 | Whitehurst et al. | |
| 7,303,525 B2 | 12/2007 | Watschke et al. | |
| 7,319,905 B1 | 1/2008 | Morgan et al. | |
| 7,328,068 B2 | 2/2008 | Spinelli et al. | |
| 7,330,764 B2 | 2/2008 | Swoyer et al. | |
| 7,343,202 B2 | 3/2008 | Mrva et al. | |
| 7,347,812 B2 | 3/2008 | Mellier | |
| 7,351,197 B2 | 4/2008 | Montpetit et al. | |
| 7,359,751 B1 | 4/2008 | Erickson et al. | |
| 7,376,467 B2 | 5/2008 | Thrope et al. | |
| 7,376,468 B2 | 5/2008 | King et al. | |
| 7,384,390 B2 | 6/2008 | Furness et al. | |
| 7,387,603 B2 | 6/2008 | Gross et al. | |
| 7,407,480 B2 | 8/2008 | Anderson et al. | |
| 7,412,289 B2 | 8/2008 | Malonek et al. | |
| 7,437,193 B2 | 10/2008 | Parramon et al. | |
| 7,450,987 B2 | 11/2008 | Varrichio et al. | |
| 7,500,945 B2 | 3/2009 | Cox et al. | |
| 7,565,198 B2 | 7/2009 | Bennett et al. | |
| 7,582,053 B2 | 9/2009 | Gross et al. | |
| 7,582,070 B2 | 9/2009 | Goode et al. | |
| 7,613,516 B2 | 11/2009 | Cohen et al. | |
| 7,628,795 B2 | 12/2009 | Karwoski et al. | |
| 7,647,113 B2 | 1/2010 | Wirbisky et al. | |
| 7,658,743 B2 | 2/2010 | Ulmsten | |
| 7,686,760 B2 | 3/2010 | Anderson et al. | |
| 7,715,920 B2 * | 5/2010 | Rondoni et al. | 607/59 |
| 7,725,197 B2 | 5/2010 | Soltis et al. | |
| 7,742,817 B2 | 6/2010 | Malinowski et al. | |
| 7,769,472 B2 * | 8/2010 | Gerber | 607/118 |
| 7,771,345 B1 | 8/2010 | O'Donnell | |
| 7,778,703 B2 | 8/2010 | Gross et al. | |
| 7,860,570 B2 | 12/2010 | Whitehurst et al. | |
| 7,890,176 B2 | 2/2011 | Jaax et al. | |
| 7,930,039 B2 | 4/2011 | Olson | |
| 8,019,443 B2 | 9/2011 | Schleicher et al. | |
| 8,052,731 B2 | 11/2011 | Soltis et al. | |
| 8,083,663 B2 | 12/2011 | Gross et al. | |
| 2001/0002441 A1 | 5/2001 | Boveja | |
| 2001/0003799 A1 | 6/2001 | Boveja | |
| 2001/0018549 A1 | 8/2001 | Scetbon | |
| 2002/0055761 A1 | 5/2002 | Mann et al. | |
| 2002/0099259 A1 | 7/2002 | Anderson et al. | |
| 2002/0147382 A1 | 10/2002 | Neisz et al. | |
| 2002/0161382 A1 | 10/2002 | Neisz et al. | |
| 2002/0165566 A1 | 11/2002 | Ulmsten | |
| 2003/0018365 A1 | 1/2003 | Loeb | |
| 2003/0023296 A1 | 1/2003 | Osypka | |
| 2003/0028232 A1 | 2/2003 | Camps et al. | |
| 2003/0060868 A1 | 3/2003 | Janke et al. | |
| 2003/0144575 A1 | 7/2003 | Forsell | |
| 2003/0171644 A1 | 9/2003 | Anderson et al. | |
| 2003/0199961 A1 | 10/2003 | Bjorklund et al. | |
| 2003/0236557 A1 | 12/2003 | Whitehurst et al. | |
| 2003/0236558 A1 | 12/2003 | Whitehurst et al. | |
| 2004/0015057 A1 | 1/2004 | Rocheleau et al. | |
| 2004/0015204 A1 | 1/2004 | Whitehurst et al. | |
| 2004/0015205 A1 | 1/2004 | Whitehurst et al. | |
| 2004/0039453 A1 | 2/2004 | Anderson et al. | |
| 2004/0059392 A1 | 3/2004 | Parramon et al. | |
| 2004/0068203 A1 | 4/2004 | Gellman et al. | |
| 2004/0093053 A1 | 5/2004 | Gerber et al. | |
| 2004/0152999 A1 | 8/2004 | Cohen et al. | |
| 2004/0242956 A1 | 12/2004 | Scorvo | |
| 2004/0248979 A1 | 12/2004 | Brettman et al. | |
| 2005/0038489 A1 | 2/2005 | Grill | |
| 2005/0043580 A1 | 2/2005 | Watschke et al. | |
| 2005/0049648 A1 | 3/2005 | Cohen et al. | |
| 2005/0055063 A1 | 3/2005 | Loeb et al. | |
| 2005/0065395 A1 | 3/2005 | Mellier | |
| 2005/0113877 A1 | 5/2005 | Spinelli et al. | |
| 2005/0113881 A1 | 5/2005 | Gross et al. | |
| 2005/0119710 A1 | 6/2005 | Furness et al. | |
| 2005/0143618 A1 | 6/2005 | Anderson et al. | |
| 2005/0149156 A1 | 7/2005 | Libbus et al. | |
| 2005/0216069 A1 | 9/2005 | Cohen et al. | |
| 2005/0228346 A1 | 10/2005 | Goode et al. | |
| 2005/0245787 A1 | 11/2005 | Cox et al. | |
| 2005/0245874 A1 | 11/2005 | Carrez et al. | |
| 2005/0250977 A1 | 11/2005 | Montpetit et al. | |
| 2005/0256367 A1 | 11/2005 | Banik | |
| 2005/0277994 A1 | 12/2005 | McNamee et al. | |
| 2005/0283235 A1 | 12/2005 | Kugler et al. | |
| 2006/0004421 A1 | 1/2006 | Bennett et al. | |

| | | | |
|---|---|---|---|
| 2006/0004429 A1 | 1/2006 | Mrva et al. | |
| 2006/0135845 A1 | 6/2006 | Kuyava et al. | |
| 2006/0149345 A1 | 7/2006 | Boggs, II et al. | |
| 2006/0241733 A1 | 10/2006 | Zhang et al. | |
| 2006/0265027 A1 | 11/2006 | Vaingast et al. | |
| 2006/0287571 A1 | 12/2006 | Gozzi et al. | |
| 2007/0021650 A1 | 1/2007 | Rocheleau et al. | |
| 2007/0027514 A1 | 2/2007 | Gerber | |
| 2007/0043416 A1 | 2/2007 | Callas et al. | |
| 2007/0100411 A1 | 5/2007 | Bonde | |
| 2007/0123952 A1 | 5/2007 | Strother et al. | |
| 2007/0179559 A1 | 8/2007 | Giftakis et al. | |
| 2007/0185541 A1* | 8/2007 | DiUbaldi et al. | 607/41 |
| 2007/0239224 A1 | 10/2007 | Bennett et al. | |
| 2007/0253997 A1 | 11/2007 | Giftakis et al. | |
| 2007/0253998 A1 | 11/2007 | Giftakis et al. | |
| 2007/0255333 A1 | 11/2007 | Giftakis et al. | |
| 2007/0255341 A1 | 11/2007 | Giftakis et al. | |
| 2007/0260288 A1 | 11/2007 | Gross | |
| 2007/0265675 A1 | 11/2007 | Lund et al. | |
| 2008/0009914 A1 | 1/2008 | Buysman et al. | |
| 2008/0033493 A1* | 2/2008 | Deckman et al. | 607/3 |
| 2008/0071321 A1 | 3/2008 | Boggs, II et al. | |
| 2008/0109045 A1 | 5/2008 | Gross et al. | |
| 2008/0114433 A1 | 5/2008 | Sage et al. | |
| 2008/0132969 A1 | 6/2008 | Bennett et al. | |
| 2008/0242918 A1 | 10/2008 | Gross et al. | |
| 2009/0012592 A1 | 1/2009 | Buysman et al. | |
| 2009/0036946 A1 | 2/2009 | Cohen et al. | |
| 2009/0043356 A1 | 2/2009 | Longhini et al. | |
| 2009/0096288 A1 | 4/2009 | Nguyen | |
| 2009/0157091 A1 | 6/2009 | Buysman | |
| 2009/0254145 A1 | 10/2009 | Gross et al. | |
| 2009/0259280 A1 | 10/2009 | Wilkin et al. | |
| 2010/0049289 A1 | 2/2010 | Lund et al. | |
| 2010/0076254 A1 | 3/2010 | Jimenez et al. | |
| 2010/0076255 A1* | 3/2010 | Robertson et al. | 600/30 |
| 2010/0114510 A1 | 5/2010 | Vaingast et al. | |
| 2010/0160716 A1 | 6/2010 | Snow | |
| 2010/0217340 A1 | 8/2010 | Watschke et al. | |
| 2011/0015738 A1 | 1/2011 | Vaingast et al. | |
| 2011/0270269 A1* | 11/2011 | Swoyer et al. | 606/129 |
| 2011/0301662 A1* | 12/2011 | Bar-Yoseph et al. | 607/40 |
| 2012/0095478 A1 | 4/2012 | Wang et al. | |

FOREIGN PATENT DOCUMENTS

| | | |
|---|---|---|
| EP | 1119314 | 8/2001 |
| EP | 1661600 | 5/2006 |
| GB | 2309388 | 7/1997 |
| JP | 52146088 | 12/1977 |
| JP | 2002521153 | 7/2002 |
| JP | 2003506145 | 2/2003 |
| JP | 2004515277 | 5/2004 |
| WO | WO9012617 | 1/1990 |
| WO | 9012617 | 11/1990 |
| WO | 9604955 | 2/1996 |
| WO | WO9604955 | 2/1996 |
| WO | 9632916 | 10/1996 |
| WO | WO9632916 | 10/1996 |
| WO | 9817190 | 4/1998 |
| WO | WO9817190 | 4/1998 |
| WO | 0000082 | 1/2000 |
| WO | 0001320 | 1/2000 |
| WO | WO0000082 A1 | 1/2000 |
| WO | WO0001320 A2 | 1/2000 |
| WO | 0006246 | 2/2000 |
| WO | 0019939 | 4/2000 |
| WO | 0019940 | 4/2000 |
| WO | WO0019939 | 4/2000 |
| WO | WO0019940 | 4/2000 |
| WO | 0110357 | 2/2001 |
| WO | WO0147440 A2 | 7/2001 |
| WO | WO0269781 A2 | 1/2002 |
| WO | 0239890 | 5/2002 |
| WO | WO0239890 A2 | 5/2002 |
| WO | 0245774 | 6/2002 |
| WO | 02069781 | 9/2002 |
| WO | 02078592 | 10/2002 |
| WO | WO02078592 A2 | 10/2002 |
| WO | 03002192 | 1/2003 |
| WO | WO03002192 A1 | 1/2003 |
| WO | WO03094693 A2 | 11/2003 |
| WO | WO2004047914 A2 | 6/2004 |
| WO | WO2005122954 A1 | 12/2005 |
| WO | WO2006014971 A2 | 2/2006 |
| WO | 2006047833 | 5/2006 |
| WO | WO2006047833 A1 | 5/2006 |
| WO | WO2006126201 A2 | 11/2006 |
| WO | WO2007025354 A1 | 3/2007 |
| WO | 2007097994 | 8/2007 |
| WO | WO2007097994 A2 | 8/2007 |
| WO | WO2007106303 A2 | 9/2007 |
| WO | 2007126632 | 11/2007 |
| WO | WO2007126632 A3 | 11/2007 |
| WO | 2007145913 | 12/2007 |
| WO | WO2007145913 A1 | 12/2007 |
| WO | WO2008057261 | 5/2008 |
| WO | WO2008121109 A1 | 10/2008 |
| WO | WO2009026078 A2 | 2/2009 |
| WO | WO2009094431 A2 | 7/2009 |
| WO | 2010107751 | 9/2010 |
| WO | WO2010107751 | 9/2010 |
| WO | WO2010107900 | 9/2010 |

OTHER PUBLICATIONS

Chai, et al., "percutaneous Scral Third nerve Root Neurostimulation Improves Symptoms and Normalizes Urinary HB-EGF Levels and Antiproliferative Activity in Patients with Interstitial Cystitis", Urology, 55(5), pp. 643-646k, May 2000.

Agazzi E., et al. "Percutaneous Tibial Nerve Stimulation and Short Latency Somatosensory Evoked Ptentials: Preliminary Reports" Eur. Urol Suppl. 2007; 6(2): 141.

Arabi, K. et al. "Implantable Multiprogrammable Microstimulator Dedicated to Bladder Control", Med. & Biol. Eng. & Comput., 1996, 34, 9-12.

Bosch, J.L. "Electrical neuromodulatory therapy in female voiding dysfunction." BJU Int. Sep. 2006;98 Suppl 1:43-8; discussion 49. Review.

Bosch, J.L.H.R, "The *Bion* Device: A Minimally Invasive Implantable Ministimulator for Pudendal Nerve Neuromodulation in Patients with Detrusor Overactivity Incontinence", Urol. Clin. N. Am 32(2005) 109-112.

Bosch, J.L.H.R, et al. "The long term effect of electrostimulation of the pelvic floor on painful bladder syndrome/interstitial cystitis patients", Neurourology and Urodynamics 2008;27(7 suppl).

Bresler, Larissa et al., "Effective Methods of Pelvic Plexus Nerve and Bladder Stimulation in Anesthetized Animal Mode" J. Rehab. Res.& Dev. 49(4) 2008 627-638.

Brindley, G.S. "Electrolytic Current-Control Elements for Surgically Implanted Electrical Devices", Med. & Biol. Eng. & Comput., 1986, 24, 439-41.

Caldwell, K.P.S. "The Use of Electrial Stimulation in Urinary Retention and Incontinence [Abridged]." Section of Urology, vol. 61, pp. 35-39, Jul. 1968.

Caldwell, K.P.S. et al. "Stress Incontinenece in Females: Report on 31 Cases Treated By Electrical Implant." J. Obstet. Gynaec. Brit. Cwlth vol. 75, pp. 777-780, Jul. 1968.

Caraballo, et al., "Sacral Nerve Stimulation as a Treatment for urge incontinence and Associated Pelvic Floor Disorders at a Pelvic Floor Center: A Follow-Up Study", Urology, 57(6 Suppl 1), p. 121, Jun. 2001.

Chai, et al., "Modified Techniques of S3 Foramen Localization and Lead Implantation in S3 Neuromodulation", Urology 58: 786-790, 2001.

Dietz et al., Mechanical Properties of Urogynecologic Implant Materials, Int. Urogynecol J. (2003) 14:239-243.

Diokno, Ananias et al., "A Simplified Method of Implanting a Neuromodulator Device" J. Urol. 169, 1466-69 2003.

Donaldson, N "Design of an Implant for Preventing Incontinence After Spinal Cord Injury", Artif Organs, vol. 32, No. 8, 2008.

Fall, et al., "Electrical Stimulation in Interstitial Cystiitis", Journal of urology 123(2), pp. 192-195, Feb. 1980.

Fall, et al., "Electrical Stimulation; A Physiologic Approach to the Treatment of Urinary Incontinence", Urologic of North America vol. 18 N. 2, May 1991 pp. 393-407.

Gaunt, RA et al., "Control of urinary bladder function with devices: successes and failures.", Prog Brain Res. 2006;152:163-94.

Green, Roger et al. "Objective Methods for Evaluation of Interferential Therapy in the Treatment of Incontinence" IEE Transactions on Biol. Eng. 37(6) 1990 615-623.

Grill WM, et al, "Emerging clinical applications of electrical stimulation: opportunities for restoration of function," J Rehabil Res Dev 2001 38(6): 641-53.

Herbison GP, et al "Sacral neuromodulation with implanted devices for urinary storage and voiding dysfunction in adults", The Cochrane Library 2009 Issue 2 1-29 (31 pages).

Ishikawa, N. et al., "Development of a non-invasive treatment system for urinary incontinence using a functional continuous magnetic stimulator (FCMS)" Med. Biol. Eng. Comput., 1998, 36, 704-10.

Kirkham, APS, "Neuromodulation through sacral nerve roots 2 to 4 with a Finetech-Brindley sacral posterior and anterior root stimulator" Spinal Cord (2002) 40, 272-81.

Medtronic "Interstim Therapy: Implant Manual" (32 pps) 2006.

Merrill, Daniel C., et al., "Treatment with Electrical Stimulation of the Pelvic Floor", Rology, Jan. 1975, vol. V, No. 1, pp. 67-72.

Odagaki, M. et al. "Comparison of Current Distribution Based on Tissue Inhomogeneity in Magnetic Stimulation for Treatment of Urinary Incontinence", IEEE Transactions on Magnetics, vol. 41, No. 10, Oct. 2005.

O'Riordan, J.M., et al. "Sacral nerve stimulation for fecal incontinence" Ir J Med Sci (2008) 177:117-119.

Petrofsky, J. "A Transurethral Electrical Stimulator", J. Clin. Eng. 17(2), 1992, 151-56.

Provost, B. "Proposed new bladder volume monitoring device based on impedance measurement", Med. Biol. Eng. Comput., 1997, 35, 691-694.

Sherman, ND, et al. "Current and future techniques of neuromodulation for bladder dysfunction", Curr Urol Rep. Nov. 2007;8(6):448-54.

Soumendra, D, et al "Sacral neurostimulation for urinary retention: 10-year experience from on UK centre" BJU International 101,192-96 (2007).

Starkman, J. et al. "Refractory overactive bladder after urethrolysis for bladder outlet obstruction: management with sacral neuromodulation", Int Urogynecol J (2008) 19:277-282.

Sutherland, S, et al. "Sacral Nerve Stimulation for Voiding Dysfunction: One Institution's 11-Year Experience", Neurourology and Urodynamics 26:19-28 (2007).

Washington, B. et al. "Implant infection after two-stage sacral nerve stimulator placement", Int Urogynecol J (2007) 18:1477-1480.

Wenzel, B. et al. "Detecting the Onset of Hyper-Reflective Bladder Contractions from the Electrical Activity of the Pudendal Nerve", IEE Trans. Neural Sys. Rehab. Eng. 13(3) 2005 428-435.

White, W., et al "Incidence and Predictors of Complications With Sacral Neuromodulation", Urology 73: 731-735, 2009.

Whiteside JL, "Lead placement and associated nerve distribution of an implantable periurethral electrostimulator." Int Urogynecol J Pelvic Floor Dysfunct. Mar. 2009;20(3):325-9.

Yamamoto et al., "Optimal parameters for effective electrical stimulation of the anal sphincters in a child with fecal incontinenece: preliminary report," Pediatr. Surg. Int. (1993) 8:132-137.

Yamanishi et al., "Electrical Stimulation for Stress incontinence", Int. Urogynecol j (1998) 9:281-290 Springer Verlag London ltd.

Zermann, et al., "Sacral nerve Stimulation for Pain Relief in Interstitial Cystitis" Urol. Int., 65(2), pp. 120-121, 2000.

Zonnervijlle, E., et al., "Dynamic graciloplasty for urinary incontinence: the potential for sequential closed-loop stimulation" Med. Eng. Phy. 25 (2003) 755-63.

Office Action from Japanese Patent Application No. 2008-557294, mailed Jan. 10, 2012.

Notification of a First Office Action from Chinese Patent Application No. 200780007709.2, mailed Sep. 27, 2010.

International Search Report and Written Opinion of PCT/US2007/004474, filed on Feb. 22, 2007.

Extended European Search Report for European Patent Application No. 10176162.5, mailed Apr. 28, 2011.

International Search Report and Written Opinion for PCT/US2011/023677, mailed Apr. 21, 2011.

International Search Report and Written Opinion for PCT/US2007/000112, filed Jan. 3, 2007.

Partial European Search Report from European Patent Application No. 10176162.5, mailed Jan. 21, 2011.

Dietz et al., "Mechanical Properties of Urogynecologic Implant Materials", Int. Urogynecol J. (2003) 14:239-243.

Iglesia et al., "The Use of Mesh in Gynecologic Surgery", Int. Urogynecol J. (1997) 8:105-115.

U.S. Appl. No. 60/578,742, filed Jun. 10, 2004.

U.S. Appl. No. 12/406,434, filed Mar. 18, 2009.

U.S. Appl. No. 60/779,219, filed Mar. 3, 2006.

Office Action from Israel Patent Application No. 162193, dated Mar. 1, 2012.

A first Communication issued by the European Patent Office for European Patent Application No. 07795734.8, dated Nov. 17, 2010.

A supplementary European Search Report for European Patent Application No. 02793278.9, dated Feb. 14, 2011.

Yamanishi et al., "Electrical Stimulation for Stress Incontinence," Int. Urogynecol J (1998) 9:281-290 Springer-Verlag London Ltd.

Yamamoto et al., "Optimal parameters for effective electrical stimulation of the anal sphincters in a child with fecal incontinence: preliminary report," Pediatr Surg Int (1993) 8:132-137.

U.S. Appl. No. 60/803,954, filed Jun. 5, 2006.

U.S. Appl. No. 60/805,036, filed Jun. 16, 2006.

Notification of a First Office Action from Chinese Patent Application No. 200780021028.1, issued Jun. 1, 2010.

Examiner's First Report from Australian Patent Application No. 2007258756, dated Jul. 22, 2011.

U.S. Appl. No. 60/091,762, filed Jul. 6, 1998.

Merrill Daniel C. et al., "Treatment with Electrical Stimulation of the Pelvic Floor", Urology, Jan. 1975, vol. V, No. 1, pp. 67-72.

Chai et al., "Percutaneous Sacral Third Nerve Root Neurostimulation Improves Symptoms and Normalizes Urinary HB-EGF Levels and Antiproliferative Activity in Patients with Interstitial Cystitis", Urology, 55(5), pp. 643-646, May 2000.

Fall et al., "Electrical Stimulation in Interstitial Cystitis", Journal of Urology, 123(2), pp. 192-195, Feb. 1980.

Zermann et al., "Sacral Nerve Stimulation for Pain Relief in Interstitial Cystitis", Urol. Int., 65(2), pp. 120-121, 2000.

Caraballo et al., "Sacral Nerve Stimulation as a Treatment for urge Incontinence and Associated Pelvic Floor Disorders at a Pelvic Floor Center: A Follow-Up Study", Urology, 57(6 Suppl 1), p. 121, Jun. 2001.

P.D. O'Donnel ed., Urinary Incontinence, Chap. 26, 1997, Mosby Publishers, St. Louis, MI pp. 197-202.

Medtronic®'s "InterStim Therapy for Urinary Control-Patient Stories", 1997, Medtronic Inc., Spring Lake Park, MN, 2 pages. (http://webprod1.medtronic.com/neuro/interstim/4Bsize.html).

Summary of Safety and Effectiveness of Medtronic® Interstim® Sacral Nerve Stimulation (SNS) TM System, Sep. 1997, Medtronic Inc., Spring Lake Park, MN, 2 pages.

Medtronic®'s InterStim Therapy for Urinary..: "for People with Bladder Control Problem", 1997, Medtronic Inc., Spring Lake Park, MN, 2 pages. (http://webprod1.medtronic.com/neuro/interstim/1types.html).

Caldwell, K.P.S. et al. "Urethral Pressure Recordings in Male Incontinents Under Electrical Stimulation." Investigative Urology vol. 5, No. 6, pp. 572-579, May 1968.

Caldwell, K.P.S. et al. "Stress Incontinence in Females: Report on 31 Cases Treated by Electrical Implant." J. Obstet. Gynaec. Brit. Cwlth vol. 75, pp. 777-780, Jul. 1968.

Caldwell, K.P.S. "The Use of Electrical Stimulation in Urinary Retention and Incontinence [Abridged]." Section of Urology, vol. 61, pp. 35-39, Jul. 1968.

Caldwell, K.P.S. "Electrical Stimulation.", Sphincter Research Unit, Royal Devon and Exeter Hospital, Exeter (England), Urol. Int. 29: 225, 1974. (1 page).

European Search Report and Written Opinion of 06011641.5 completed Aug. 21, 2006.

* cited by examiner

MULTI-ZONE STIMULATION IMPLANT
SYSTEM AND METHOD

FIELD OF THE INVENTION

The present invention relates generally to surgical methods and apparatus and, more specifically, to surgical implants or mesh having multiple stimulation zones defined therein.

BACKGROUND OF THE INVENTION

Pelvic health for men and women is a medical area of increasing importance, at least in part due to an aging population. Examples of common pelvic ailments include incontinence (e.g., fecal and urinary), pelvic tissue prolapse (e.g., female vaginal prolapse), and conditions of the pelvic floor.

Urinary incontinence can further be classified as including different types, such as stress urinary incontinence (SUI), urge urinary incontinence, mixed urinary incontinence, among others. Other pelvic floor disorders include cystocele, rectocele, enterocele, and prolapse such as anal, uterine and vaginal vault prolapse. A cystocele is a hernia of the bladder, usually into the vagina and introitus. Pelvic disorders such as these can result from weakness or damage to normal pelvic support systems.

Urinary incontinence can be characterized by the loss or diminution in the ability to maintain the urethral sphincter closed as the bladder fills with urine. Male or female stress urinary incontinence (SUI) generally occurs when the patient is physically stressed.

In its severest forms, vaginal vault prolapse can result in the distension of the vaginal apex outside of the vagina. An enterocele is a vaginal hernia in which the peritoneal sac containing a portion of the small bowel extends into the rectovaginal space. Vaginal vault prolapse and enterocele represent challenging forms of pelvic disorders for surgeons. These procedures often involve lengthy surgical procedure times.

Urinary incontinence can be characterized by the loss or diminution in the ability to maintain the urethral sphincter closed as the bladder fills with urine. Male or female stress urinary incontinence (SUI) occurs when the patient is physically stressed.

U.S. Pat. Nos. 6,354,991 and 6,896,651 to Gross et al., which are incorporated herein by reference, describe a device and method for treatment of urinary stress incontinence. At least one electrode is implanted in a pelvic muscle of a patient. A control unit receives signals indicative of abdominal stress in the patient and responsive thereto applies an electrical waveform to the electrode which stimulates the muscle to contract, so as to inhibit involuntary urine flow through the patient's urethra due to the stress. U.S. Pat. No. 6,652,449 to Gross et al., which is incorporated herein by reference, describes a device for treatment of a patient's urinary incontinence, including a sensor, which generates a signal responsive to a physiological characteristic indicative of a likelihood of incontinence. A control unit receives the signal from the sensor. At least one electrode is preferably implanted in the patient. The electrode is coupled to cause contraction of the pelvic muscle of the patient responsive to application of electrical energy to the electrode. Responsive to the signal, the control unit applies an electrical waveform to the electrode, so as to inhibit the incontinence.

U.S. Patent Publication No. 2007/0260288 and PCT Patent Publication Nos. WO 2007/106303 and WO 2007/145913, which are hereby incorporated herein by reference, disclose various active implantable stimulation devices having one or more electrodes and a control unit adapted to drive the one or more electrodes to apply current to pelvic tissue, such as the rectum and urethra.

There is a desire to obtain improved fixation of implants, anchors, or stimulation leads within the body of the patient.

SUMMARY OF THE INVENTION

The present invention describes pelvic mesh implants, stimulation leads or systems, and methods for treating pelvic conditions such as incontinence (various forms such as fecal incontinence, stress urinary incontinence, urge incontinence, mixed incontinence, etc.), vaginal prolapse (including various forms such as enterocele, cystocele, rectocele, apical or vault prolapse, uterine descent, etc.), and other conditions caused by muscle and ligament weakness.

Certain embodiments can include a mesh implant adapted for pelvic floor stimulation. In one embodiment, a support structure, e.g., mesh sling or implant, one or more stimulation elements, and an energizing element are included. Leads or electrodes can be positioned in desired stimulation zones of the implant. As such, the implant can include multiple electrically isolated mesh electrode pads.

BRIEF DESCRIPTION OF THE DRAWINGS

The above summary and its identified advantages will become apparent to those skilled in the art to which the invention pertains upon further consideration of the example embodiments depicted and described in the following, to which.

DETAILED DESCRIPTION OF PREFERRED
EMBODIMENTS

Figure 1:
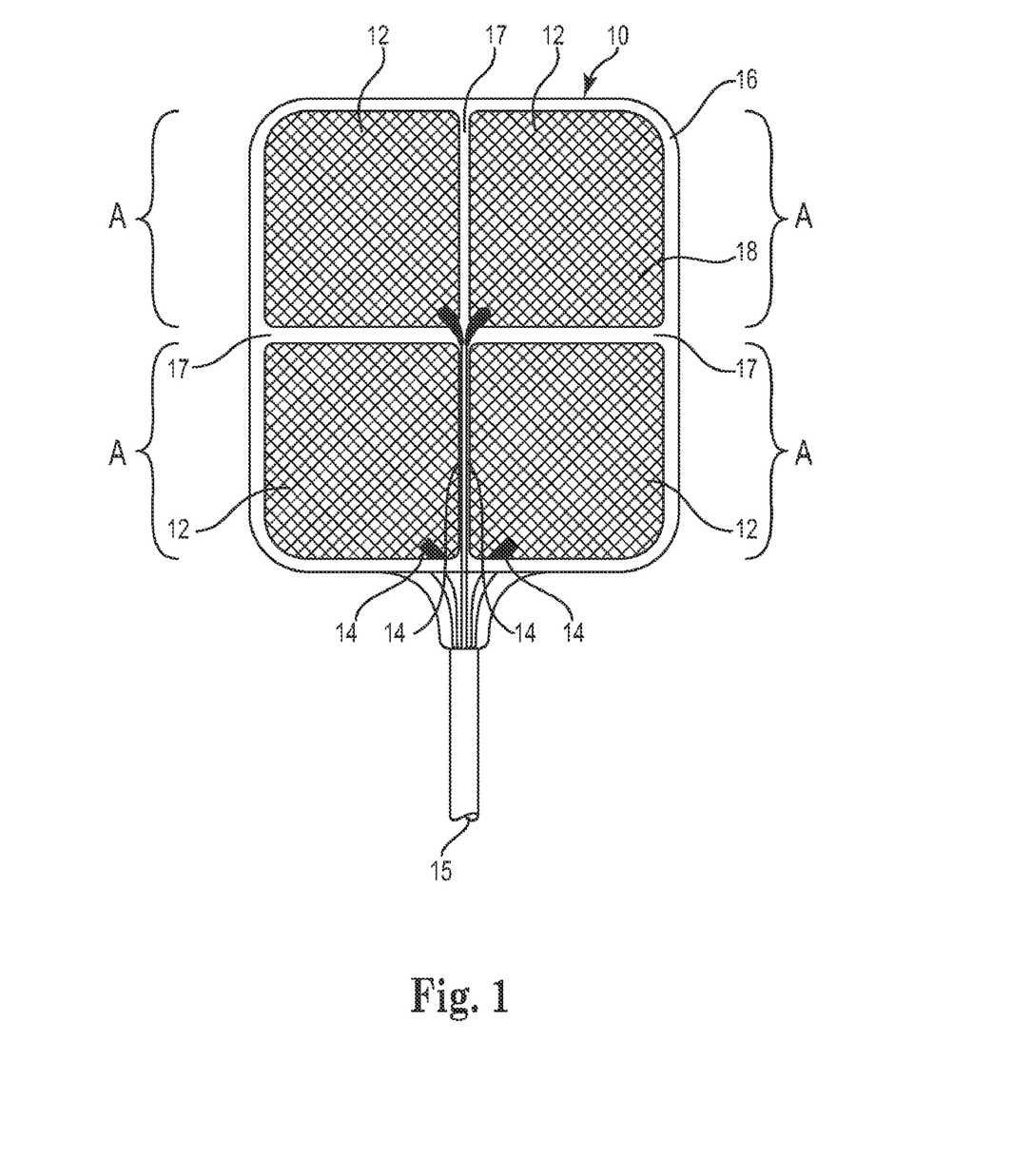
FIG. 1 depicts a multi-zone mesh implant for stimulation and fixation in accordance with embodiments of the present invention.
Figure 2:
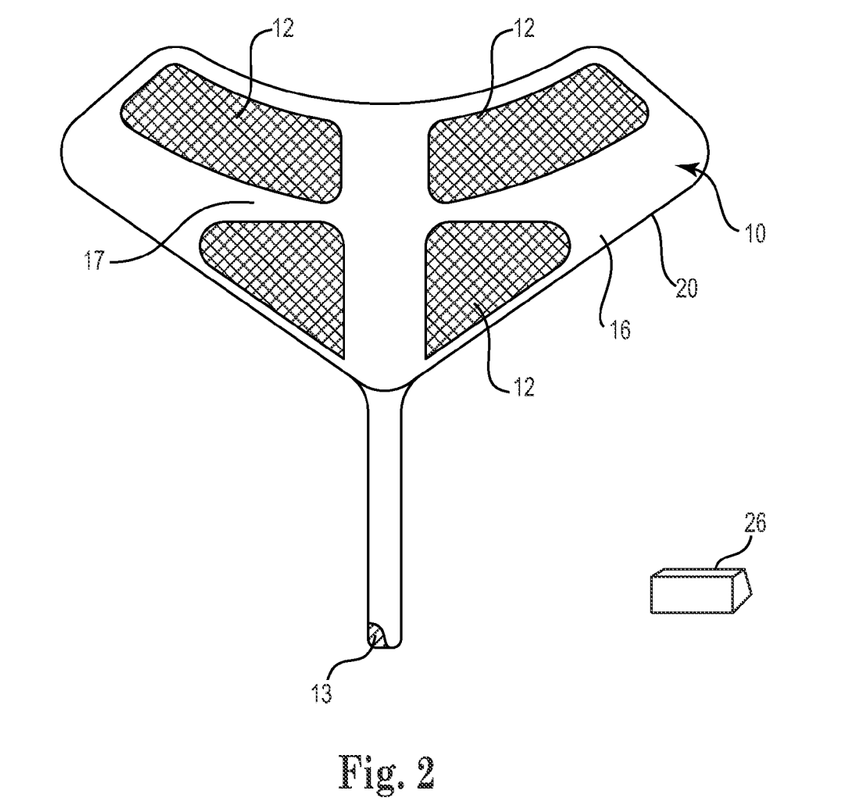
FIG. 2 depicts a multi-zone mesh implant for stimulation and fixation having a generally contoured configuration.
Figure 3:
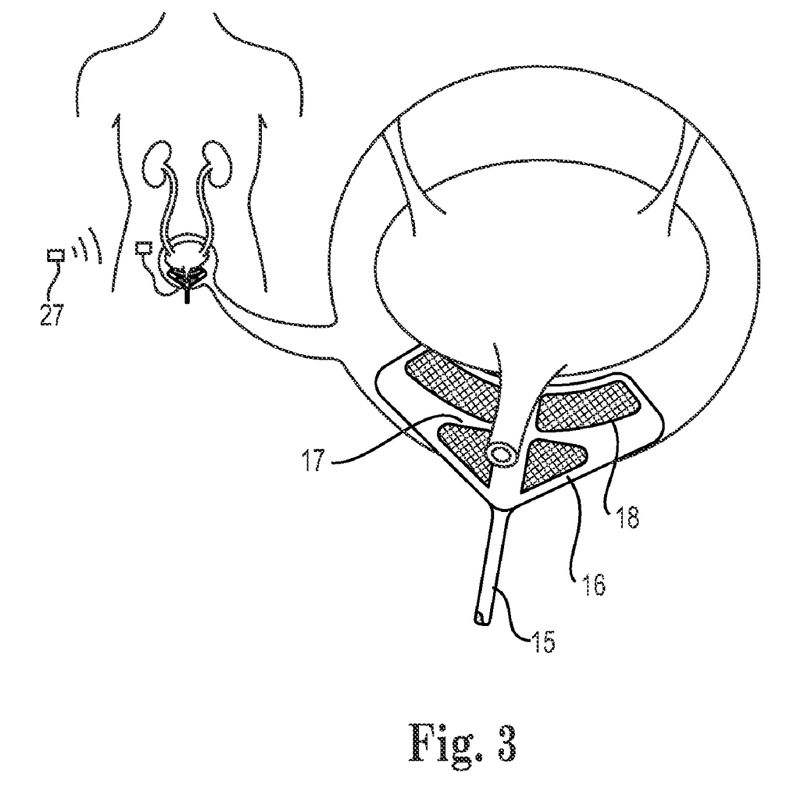
FIG. 3 depicts a multi-zone mesh implant for stimulation and fixation in a contoured configuration proximate a patient's bladder.

Referring generally to FIGS. 1-3, example embodiments are shown of an incontinence control implant system 10 capable of being generally contoured or conformed to pelvic organs or tissue within a patient's pelvic cavity. One of the many features of the invention is its ability to provide mechanical support while stimulating nerve and muscle tissue. Implant 10 is designed to generally have a shape and surface area that allows it to come into contact with the nerves and/or muscles of incontinence control structures such as the bladder, urethra, pelvic muscle, bowel and/or rectal tissue.

In one embodiment, implant system 10 has a support structure 12, e.g., mesh (woven or non-woven) sling or implant that supports the organ or tissue, one or more stimulation elements 14 (e.g., leads) that stimulates the nerves or muscle, and an energizing element 15 that transmits a stimulus to the stimulation elements 14. Leads or electrodes 14 can be positioned in desired stimulation zones of implant 10. As such, implant 10 can include multiple isolated conductive electrode pads, patches, regions or zones identified in the figures by the letter A.

Referring particularly to the example embodiment depicted in FIG. 1, zones A are defined within support structure 12 of implant system 10 by one or more frame portions 16 that supports and separates one or more mesh portions 18. Frame portions 16 can separate mesh portions 18 into any of a number of stimulation zones A. In FIG. 1, for example, four stimulation zones A are illustrated. One skilled in the art, however, would understand that implant 10 can be fabricated with any number of stimulation zones.

Turning now to frame portions 16, example embodiments are contemplated having frame portions 16 extending about a perimeter of support structure 12. Intersecting support portions 17 can extend away from the perimeter and either connect with another portion of the perimeter or intersect another intersecting support portion 17. One or more intersecting support portions 17 can extend away from the perimeter. Frame portions 16 and intersecting support portions 17 can be fabricated from any biologically compatible material such as, for example, polypropylene or silicone. Frame 16 portions and intersecting support portions 17 can also be porous or non-porous and rigid, semi-rigid or flexible.

In one embodiment, as illustrated in FIGS. 2 and 3, support structure 12 can be flexed, bent or conformed to the shape of an organ or tissue to be supported and/or stimulated. In an example embodiment, frame portions 16 and the intersecting support portions 17 can be flexed, bent, contoured or molded into a particular shape by a physician so that implant 10 can be placed in contact with the contour of an organ or tissue. Frame portions 16 and intersecting support portions 17 can be fabricated from any material that can retain a particular shape, for example, nitinol and similar wires. In some example embodiments, the material used to retain a particular shape can be coated or covered by frame portions 16 or intersecting support portions 17. Silicone or other like materials can also be provided around the edges or between predetermined stimulation zones A of implant 10 to provide zone separation and to protect from erosion potential.

As illustrated in FIGS. 1-3, mesh portions 18 can be disposed between frame portions 16 and intersecting support portions 17. Mesh portions 18 are generally porous to allow tissue ingrowth and to prevent movement of implant 10 once placed into the patient. Mesh portions 18 can be woven or generally non-woven. Support structure 12, as a whole or in portions, can be fabricated from a molding process, laser cutting or weaving. In another embodiment, mesh portions 18 can also be fabricated from a material similar to frame portions 16 and intersecting support portions 17 that allows it to retain a particular shape.

The shape of implant 10 or pad can vary greatly in geometry and size to better control target stimulation zones for specific anatomical areas of tissue. The shape can also be predetermined during the fabrication process to eliminate or reduce the need of the physician to mold or conform implant 10 to the patient's anatomy. While four zones are generally depicted in the figures, any numbers of zones, zone shapes, and zone configurations can be implemented with the present invention.

Stimulation leads 14 can be selectively placed anywhere along the mesh portions 18 or stimulation zones A during the fabrication process. In one embodiment, mesh portions 18 are made from a conductive material that transfers or carries the signal from stimulation lead 14 through the stimulation zone A. The flexibility of implant 10 allows it to wrap around or generally abut or surround the potential target tissue or zone A to be stimulated. This provides a distinct advantage over previous methods that attempted to merely place an elongate lead adjacent a nerve. Implant 10 allows a greater area of the organ or tissue to be stimulated, thereby eliminating the need for pinpoint precision. Implant 10 is also capable of having tissue ingrowth into mesh portions 18, thereby eliminating the concern of lead migration in the patient.

Mesh portions 18 of implant 10 can also have a particular geometry that permits it to expand, contract, stretch, shrink and the like. The particular geometry may permit implant 10 to better conform to the organ or tissue to be stimulated. The space or size of the pores may be uniform or non-uniform across mesh portions 18. The particular geometry may also assist in the mechanical support of the organ or tissue.

Implant 10 can also have an insulative back layer 20 that insulates and protects the tissue opposite the organ or tissue to be stimulated. Any non-conductive and biocompatible material may be used during the fabrication process. For instance, silicone, rubber or another layer of polypropylene can be used. Insulative layer 20 can be connected to the non-stimulating side of implant 10 by adhesives, molding, welding and the like known to those skilled in the art.

Implant 10 of the present invention also has a control module 26 in operative communication with support structure 12 to control the transmission of the electric current to and through support structure 12. Control module 26 can be implanted into the patient and controlled by a remote control 27. Remote control 27 makes implant 10 electrically active, with stimulation zones A controlled to maximize effectiveness of the stimulation. Zones A within the mesh may be turned on or off independently of one another to adjust stimulation characteristics at the target tissue or zone. The amplitude of the stimulation may also be varied among the zones A to permit the user or a physician to maximize the control of incontinence.

Figure 4:
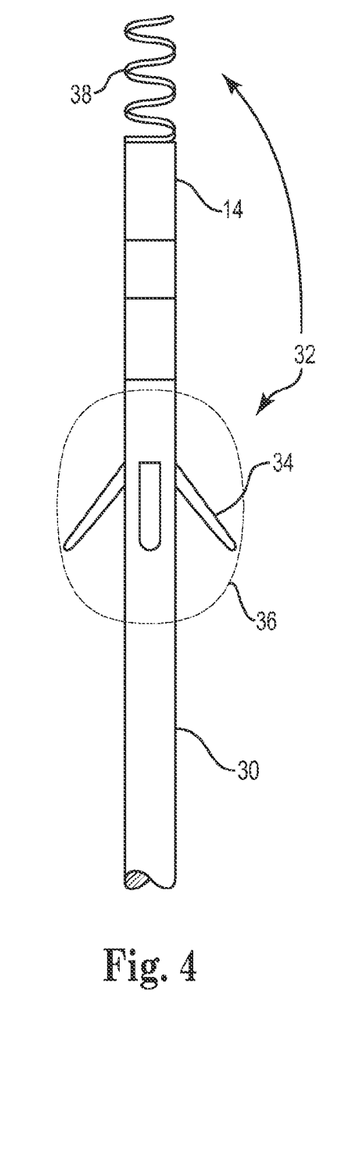
FIG. 4 depicts an example embodiment of an anchor disposed on a portion of an implant to prevent movement of the implant in the body.

Alternate embodiments of implant 10 also combine the fixation characteristics of mesh with the ability of precision control of the desired area of stimulation. As such, the electrically active mesh can provide both fixation (tissue in-growth) and electrical stimulation (electrode treatment) benefits. As shown in FIGS. 4-8, embodiments of lead 14 can include a sleeve 30. Sleeve 30 can further include one or more fixation devices 32 attached thereto or therealong. Fixation devices 32, in one embodiment, are generally helical or barb in shape or they can include a plurality of extending and/or angled tines 34. Fixation devices 32 can be provided or otherwise incorporated with sleeve 30 or lead 14 anywhere along the length of the sleeve or lead. Such a helical fixation device 32 can provide resistance to back turning and undesirable movement of lead 14 during insertion, placement and deployment of the system. As illustrated in FIG. 4, fixation device 32 can be in multiple locations on a particular lead 14.

Figure 5:
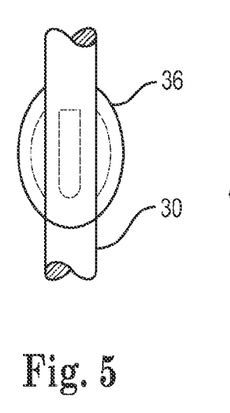
FIG. 5 depicts the anchor of FIG. 4 encased in a dissolvable casing.

In some embodiments, a soluble capsule or casing 36 is provided that surrounds, encases or envelops at least a portion of one or more expandable fixation devices or anchors 32. Expandable fixation anchors 32 can be configured with various known barbs or tines 34, or like elements to promote tissue fixation.

Figure 6:
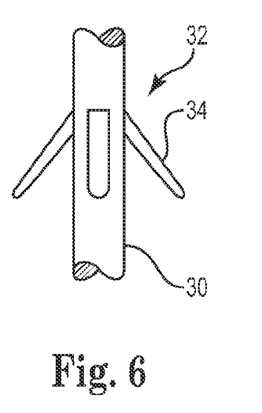
FIG. 6 depicts the anchor of FIG. 5 in an expanded position after the casing has dissolved.

During initial insertion within the body of the patient, capsule 36 encases expandable fixation devices 32 such that tines 34 lay in a generally flat orientation. When capsule 36 dissolves (e.g., automatically, upon application of dissolving agent or substance, or by way of an environmental condition naturally occurring in a patient's body), tines 34 extending therefrom, are released from their flat restrictive state such that tines 34 can engage tissue for fixation. Various levels of dissolvability can be provided with capsule 36 to provide desired or predetermined release of expandable fixation devices 32. The expandable fixation devices 32, or portions thereof, can be constructed of various compatible flexible materials, such as known polymers or metals.

Figure 7:
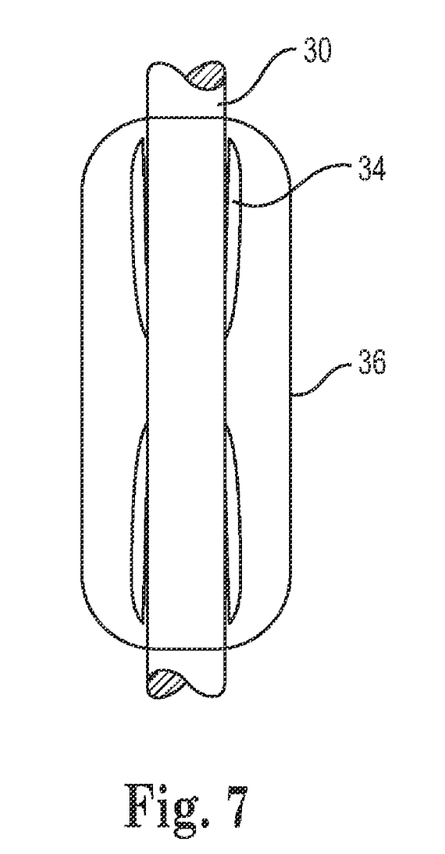
FIG. 7 depicts another example embodiment of an anchor in a retracted position.
Figure 8:
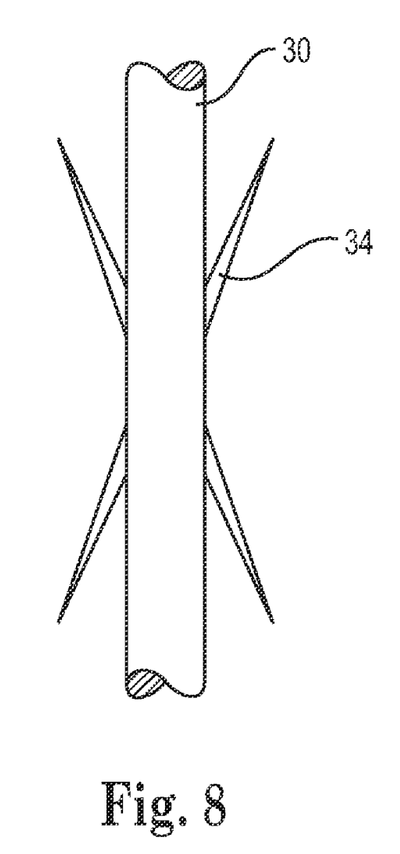
FIG. 8 depicts the anchor of FIG. 7 in an expanded position.

In certain embodiments, as shown in FIGS. 4, 5 and 7, a temperature sensitive adhesive or other known substance can be used to restrict tines 34 in a deployable flat position until a desired or predetermined condition or variable dissolves or otherwise releases the substance to thereby release the tines 34 for fixation. In the example embodiment of FIG. 7, multiple tines 34 can be deployed that extend in opposite directions relative to each other to ensure that lead 14 does not move in any direction.

The embodiment of FIG. 4 illustrates a lead 14 having a sleeve 30 with a helical tip 38. Tip 38 can be adapted (based on shape and material construct) to be in a generally compressed state while lead 14 is placed in a patient. Once placed, tip 38 can spring or expand back to its extended position to resist pull back of sleeve 30 and/or lead 14. Other like design configuration to promote insertion while still facilitating fixation or limiting undesired movement after insertion are envisioned for the sleeve and/or lead as well.

In various embodiments, sleeve 30 and fixation devices 32 of the present invention can be employed with mesh implant or slings to provide advantageous anchoring with target tissue of the patient.

The systems, their various components, structures, features, materials and methods of the present invention may have a number of suitable configurations as shown and described in the previously-incorporated references. Various methods and tools for introducing, deploying, anchoring and manipulating implants or stimulation leads to treat incontinence and prolapse as disclosed in the previously-incorporated references are envisioned for use. The various implant systems 10, features and methods detailed herein are envisioned for use with many known implant, stimulation and repair systems (e.g., for male and female), features and methods, including those disclosed in U.S. Pat. Nos. 7,500,945, 7,407,480, 7,351,197, 7,347,812, 7,303,525, 7,267,645, 7,025,063, 6,911,003, 6,691,711, 6,648,921, and 6,612,977, International Patent Publication Nos. WO 2008/057261 and WO 2007/097994, and U.S. Patent Publication Nos. 2002/151762, 2002/0161382, 2007/0260288, and 2002/147382. Accordingly, the above-identified disclosures are fully incorporated herein by reference in their entirety, with each of the identified publications being incorporated herein by reference in their entirety. As detailed above, the deployable fixation features or anchors can be utilized to selectively anchor leads, implants, or other treatment devices or elements adapted for treating incontinence, prolapse and like conditions.

All patents, patent applications, and publications cited herein are hereby incorporated by reference in their entirety as if individually incorporated, and include those references incorporated within the identified patents, patent applications and publications.

Obviously, numerous modifications and variations of the present invention are possible in light of the teachings herein. It is therefore to be understood that within the scope of the appended claims, the invention may be practiced other than as specifically described herein.

The invention claimed is:

1. An implant stimulation system for stimulating tissue of a pelvic region, said system comprising:
    a formable support structure having a plurality of stimulation zones capable of independently stimulating different areas of a pelvic region, the support structure comprising frame portions separating the stimulation zones that is formable to the tissue being stimulated, the stimulation zones comprising mesh portions connected to the frame portions;
    at least one lead being in operative communication with each stimulation zone; and
    a control module in operative communication with the at least one lead to control the stimulus to each of the stimulation zones.

2. The stimulation system of claim 1, further comprising a remote control in operative communication with the control module to allow a user or physician to control the stimulus to the stimulation zones.

3. The stimulation system of claim 1, wherein the mesh portion comprises a conductive material to spread the stimulus over the area of the stimulation zone.

4. The stimulation system of claim 1, wherein the mesh portion comprises pores having a uniform opening across the stimulation zones.

5. The stimulation system of claim 1, wherein the mesh portion comprises pores having a non uniform opening across the stimulation zones.

6. The stimulation system of claim 1, wherein the stimulation zones are simultaneously stimulated.

7. The stimulation system of claim 1, wherein the stimulation zones are selectively stimulated by a user or physician.

8. The stimulation system of claim 1, further comprising at least one fixation device being coupled to at least one of the leads to prevent movement of the lead in a patient.

9. The stimulation system of claim 8, wherein the fixation device comprises one or more tines extending angularly away from the lead.

10. The stimulation system of claim 8, further comprising a capsule encasing at least one fixation device in a collapsed state.

11. The stimulation system of claim 10, wherein the capsule is dissolvable to permit the fixation device to move from a collapsed state to an expanded state.

12. An implant stimulation system for stimulating tissue of a pelvic region, said system comprising:
    at least one lead being in operative communication with an organ or tissue of a pelvic region;
    a helical anchor disposed on a tip of the lead;
    a dissolvable capsule encasing the helical anchor and retaining the helical anchor in a compressed state and allowing the helical anchor to expand to an expanded state upon dissolving; and
    a control module in operative communication with the at least one lead to control the stimulus thereto.

* * * * *